(12) United States Patent
Ober et al.

(10) Patent No.: US 8,701,469 B2
(45) Date of Patent: Apr. 22, 2014

(54) FLEXIBLE SUBSTRATE SENSOR SYSTEM FOR ENVIRONMENTAL AND INFRASTRUCTURE MONITORING

(75) Inventors: Christopher Kemper Ober, Ithaca, NY (US); Thomas Denis O'Rourke, Ithaca, NY (US); Michael G. Spencer, Ithaca, NY (US); James N. Turner, Delmar, NY (US); Stephen B. Wicker, Ithaca, NY (US)

(73) Assignees: Cornell University, Ithaca, NY (US); Health Research, Inc., Menands, NY (US)

( * ) Notice: Subject to any disclaimer, the term of this patent is extended or adjusted under 35 U.S.C. 154(b) by 287 days.

(21) Appl. No.: 12/515,718

(22) PCT Filed: Nov. 19, 2007

(86) PCT No.: PCT/US2007/024226
§ 371 (c)(1),
(2), (4) Date: Jan. 27, 2010

(87) PCT Pub. No.: WO2008/140490
PCT Pub. Date: Nov. 20, 2008

(65) Prior Publication Data
US 2011/0283821 A1 Nov. 24, 2011

Related U.S. Application Data

(60) Provisional application No. 60/860,366, filed on Nov. 21, 2006.

(51) Int. Cl.
*G01N 37/00* (2006.01)
(52) U.S. Cl.
USPC .......................................... 73/61.41; 73/61.58

(58) Field of Classification Search
USPC ......... 73/53.01, 53.05, 61.41, 61.58, 862.621
See application file for complete search history.

(56) References Cited

U.S. PATENT DOCUMENTS 4,503,705 A * 3/1985 Polchaninoff ................... 73/172
4,697,456 A * 10/1987 Maser ............................. 73/592

(Continued)

FOREIGN PATENT DOCUMENTS

DE    10240446 A1 * 3/2004 ............. G08C 17/02
JP    04038432 A  * 2/1992 ................. G01L 1/20

(Continued)

OTHER PUBLICATIONS

Lynch et al., "The Design of a Wireless Sensing Unit for Structural Health Monitoring", Proceedings of the 3rd International Workshop on Structural Health Monitoring, Sep. 12-14, 2001.*

(Continued)

*Primary Examiner* — David A Rogers
(74) *Attorney, Agent, or Firm* — Harris Beach PLLC

(57) ABSTRACT

A sensor system utilizing flexible electronics for on-line real-time high-sensitivity sampling, monitoring, and analysis of a parameter or analyte of interest in a fluid or in or on a solid is provided. The flexible substrate sensor system comprises a plurality of sensors, a flexible substrate, a network, and a connection between the sensors and the network, wherein the network reads out or collects information from the sensors. The network can be onboard, connected by via a physical connection to the sensors and the flexible substrate, or external to the sensors and flexible substrate, connected via a telemetric or wireless connection to the sensors. The flexible substrate sensor system can be deployed in systems that conduct or distribute fluids or solids, such as distribution systems (municipal water systems, oil or gas pipeline systems), industrial systems (production facilities, piping, and storage systems), and large structures (dams, bridges, walkways, buildings).

41 Claims, 10 Drawing Sheets

(56) References Cited

U.S. PATENT DOCUMENTS

| | | | | |
|---|---|---|---|---|
| 4,972,105 | A | * | 11/1990 | Burton et al. .................. 326/39 |
| 5,347,871 | A | * | 9/1994 | D'Andrea et al. .............. 73/775 |
| 5,981,268 | A | * | 11/1999 | Kovacs et al. ............. 435/287.1 |
| 6,127,672 | A | * | 10/2000 | Danisch ................... 250/227.14 |
| 6,322,963 | B1 | * | 11/2001 | Bauer ............................. 435/4 |
| 6,649,403 | B1 | | 11/2003 | McDevitt et al. |
| 6,990,860 | B1 | * | 1/2006 | Gillanders ..................... 73/149 |
| 7,034,660 | B2 | * | 4/2006 | Watters et al. ............. 340/10.41 |
| 7,187,299 | B2 | * | 3/2007 | Kunerth et al. .......... 340/870.05 |
| 7,498,802 | B2 | * | 3/2009 | Takahata ................. 324/207.15 |
| 7,501,301 | B2 | * | 3/2009 | Kovacs et al. .................. 438/49 |
| 7,690,246 | B1 | * | 4/2010 | Discenzo .................... 73/53.05 |
| 7,698,962 | B2 | * | 4/2010 | LeFebvre et al. ........ 73/862.621 |
| 7,705,725 | B2 | * | 4/2010 | Matsen et al. ................. 340/529 |
| 2002/0028110 | A1 | * | 3/2002 | Rhee et al. ................. 405/129.5 |
| 2002/0032867 | A1 | | 3/2002 | Kellum |
| 2002/0124643 | A1 | * | 9/2002 | Robinson ................... 73/290 R |
| 2002/0127623 | A1 | * | 9/2002 | Minshull et al. ............. 435/7.92 |
| 2003/0198517 | A1 | * | 10/2003 | Kostelnik et al. ........ 405/129.57 |
| 2004/0056016 | A1 | * | 3/2004 | Tian et al. ..................... 219/408 |
| 2004/0078219 | A1 | * | 4/2004 | Kaylor et al. ..................... 705/2 |
| 2004/0102803 | A1 | * | 5/2004 | Boecker et al. ............... 606/183 |
| 2004/0107065 | A1 | * | 6/2004 | Al-Ali .......................... 702/104 |
| 2005/0120778 | A1 | * | 6/2005 | Von Herzen et al. ........ 73/61.41 |
| 2005/0137833 | A1 | * | 6/2005 | Sistla ............................ 702/188 |
| 2005/0255724 | A1 | * | 11/2005 | Picco et al. ..................... 439/77 |
| 2006/0055392 | A1 | | 3/2006 | Passmore et al. |
| 2006/0056161 | A1 | * | 3/2006 | Shin et al. ..................... 361/749 |
| 2006/0154398 | A1 | * | 7/2006 | Qing et al. ...................... 438/48 |
| 2006/0158181 | A1 | * | 7/2006 | Shoji ............................. 324/240 |
| 2006/0254369 | A1 | | 11/2006 | Yoon et al. |
| 2007/0018083 | A1 | * | 1/2007 | Kumar et al. ............ 250/227.14 |
| 2007/0090059 | A1 | * | 4/2007 | Plummer et al. .............. 210/743 |
| 2007/0095160 | A1 | * | 5/2007 | Georgeson et al. ............. 73/866 |
| 2007/0096904 | A1 | * | 5/2007 | Lockyer et al. ............ 340/545.1 |
| 2007/0179730 | A1 | * | 8/2007 | Bornhoevd et al. ........... 702/116 |
| 2008/0064941 | A1 | * | 3/2008 | Funderburk et al. .......... 600/347 |
| 2009/0273909 | A1 | * | 11/2009 | Shin et al. ..................... 361/749 |
| 2009/0308742 | A1 | * | 12/2009 | Paranjape .................. 204/403.1 |
| 2010/0234997 | A1 | * | 9/2010 | Sandini et al. ................ 700/258 |

FOREIGN PATENT DOCUMENTS

| | | | | | |
|---|---|---|---|---|---|
| JP | 04283602 | A | * | 10/1992 | ............. G01B 7/18 |
| JP | 11051953 | A | * | 2/1999 | ............... G01P 5/12 |
| JP | 2000233163 | A | * | 8/2000 | ............... B09B 1/00 |
| JP | 2000258278 | A | * | 9/2000 | ............. G01M 3/04 |

OTHER PUBLICATIONS

Kollios, George, et al. "Robust aggregation in sensor networks." IEEE Data Engineering Bulletin 28.1 (2005): 26-32.*

Hill, Jason L., "System Architecture for Wireless Sensor Networks", University of California—Berkeley, 2003.*

Tan, Hwee-Xian, "Quality of Service in Wireless Sensor Networks", Apr. 17, 2006.*

International Search Report and Written Opinion of the International Searching Authority for PCT/US2007/024226 mailed Nov. 7, 2008 (8 pgs.).

* cited by examiner

Water Main

FLEXIBLE SUBSTRATE SENSOR SYSTEM FOR ENVIRONMENTAL AND INFRASTRUCTURE MONITORING

CROSS REFERENCE TO RELATED APPLICATIONS

This application is a national stage application under 35 U.S.C. §371 of PCT Application No. PCT/US07/024,226 filed Nov. 19, 2007, which claims priority to and the benefit of U.S. provisional patent application Ser. No. 60/860,366 entitled "Flexible Substrate Sensor System for Environmental and Infrastructure Monitoring," filed Nov. 21, 2006, which is incorporated herein by reference in its entirety.

STATEMENT REGARDING FEDERALLY SPONSORED RESEARCH OR DEVELOPMENT

The disclosed invention was made with government support under Contract No. NSF ANI 0325556 from the National Science Foundation Information Technology Research for National Priorities (ITR) Program. The government has rights in this invention.

TECHNICAL FIELD

The present invention relates to flexible substrate sensor, analysis, networking and communications systems for detecting and measuring parameters or analytes of interest. The invention also relates to sensor systems for monitoring environmental, structural, mechanical or infrastructure parameters, and for analysis, networking and communication of information related to the sensor measurements.

BACKGROUND OF THE INVENTION

It is often necessary to detect or measure a low concentration of a substance or parameter of interest and to communicate the data or analyze and communicate the result as effectively as possible. While sensors often exist for sensing a given chemical or biological analyte, or a physical or chemical parameter, it is often difficult or impossible to accurately or reliably detect or measure such analytes or parameters in a fluid or in (or on) a solid. This is in part due to the inability of currently available detection systems to sample a large enough volume of a fluid or solid, much less all of the fluid or solid. Current systems either sacrifice sensitivity to sample a large volume or sample a much smaller volume at the required sensitivity. The result is either that the sensitivity is too low to detect the analyte(s) or parameter(s) at the required (often regulated) level, or the smaller volume is not representative of the larger volume that needs to be thoroughly interrogated. Thus, it is too expensive, too time consuming or impossible to perform the required analysis at the level required with present technology. Further, present systems are limited in their abilities to transfer information, for example, from sensors to either onboard and/or external devices, so that the information can be analyzed and reported, and are limited in their ability to determine or to report the status of one or more sensors. Current systems are also limited in their ability to reduce communication costs through onboard computation, for example, in the form of data fusion and aggregation.

There is therefore a need in the art for a sensitive power-, computation-, and communication-efficient system for detecting an analyte, parameter or mechanical or structural characteristic of interest in a fluid or in (or on) a solid and for transferring information about the analyte, parameter or characteristic to an onboard or external device for analysis. This need is acute for large fluid volumes, or large systems or structures, especially when high sensitivity is required.

Citation or identification of any reference in this section, or in any other section of this application, shall not be considered an admission that such reference is available as prior art to the present invention.

SUMMARY OF THE INVENTION

A sensitive and efficient flexible substrate sensor system is provided for detecting a parameter (including a structural or mechanical characteristic) or analyte of interest in a fluid or in (or on) a solid and for analyzing and/or communicating the resultant information. Such information can include, for example, sensor measurements and/or the result of onboard analysis of these measurements.

The term "fluid", as used herein, refers to any fluid, whether in liquid or gaseous form, or more generally, any substance that deforms continuously under the action of an applied shear force or stress.

Also provided is a flexible substrate sensor system that can conform to the specific geometry of a measurement environment or condition of interest, and that can rapidly and efficiently transfer or communicate information about a parameter, analyte or characteristic of interest to an onboard device or an external device for analysis. In one embodiment, both an onboard analysis device and an external analysis device can be used in combination. Also provided is a flexible substrate sensor system for monitoring environmental or infrastructure parameters. In one embodiment, the flexible substrate sensor system can monitor a physical characteristic or a response of a solid mechanical or structural system.

A flexible substrate sensor system for detecting a parameter, analyte or characteristic of interest in a fluid or in (or on) a solid is also provided. In one embodiment, the flexible substrate sensor system can comprise a plurality of sensors, a flexible substrate, a network, and a connection between the sensors and the network, wherein the network reads out the sensors or collects information from the sensors. In another embodiment, the network can be onboard, i.e., associated with the plurality of sensors and/or flexible substrate and connected via a physical connection to the sensors and the associated flexible substrate. In another embodiment, the network can be located external to the sensors and flexible substrate and is connected to the sensors via a telemetric or wireless connection.

Also provided are systems and methods for performing a computation regarding a parameter, analyte or characteristic of interest, onboard or externally, and both after or before networking, onboard, externally or both.

In one embodiment, a flexible substrate sensor system is provided that is capable of conforming to the geometry of the material or system being measured to bring a plurality of sensors in a regular or random array into contact with a material so as to sense the analyte or parameter being measured. The analyte of interest or the material comprising the analyte of interest can be a fluid (e.g. a liquid fluid or a gaseous fluid) or a solid.

In one embodiment, the material comprising the analyte of interest can be a component of the fluid or solid in which the analyte of interest exists. In another embodiment, the material can be a component that a measured parameter describes. One non-limiting example of an analyte of interest is a chemical or biological agent in a public water system. Other non-limiting examples of a measured parameter of interest are pH or temperature of water in a public water system or strain in a concrete structure.

In another embodiment, a plurality of flexible substrate sensors can be arranged on a sheet of flexible substrate such that each array constitutes a complete measurement array for a desired application.

Also provided is a method for replacing defective or saturated sensors, or analysis or communication components or system(s), in a flexible substrate sensor system. In one embodiment, a sheet of flexible substrate can have a plurality of sensor arrays and electronics that are disposed (e.g., rolled up or wound) on the sheet so that only one array (the "working" array) is presented or exposed to the system being measured, whereas used (exposed) or defective arrays and/or unexposed arrays can be stored or sequestered so that they are not presented. According to this embodiment, the working sensor array can be replaced by advancing or translocating the sheet so as to expose a new array to the system being measured.

In another embodiment, a plurality of sensors can be situated on the flexible substrate as an array of individual sensors such that the measurement performed by each sensor in the array is independent of the others. In another embodiment, a subset or all of the sensors can be connected via an onboard network to provide an integrated measurement.

In another embodiment, sensors for multiple analytes, parameters, or characteristics, or any combination of analytes and/or parameters and/or characteristics, can be multiplexed into an array of sensors with any desired organization of the sensors known in the art. For example, there can be any number of sensors sensing each analyte or parameter, and the juxtaposition and the ratio of the number of different types of sensors can be whatever is known in the art as being best suited to the contemplated application.

In another embodiment, the connection can connect the flexible substrate sensor system to an onboard analysis device. In another embodiment, the connection can connect the flexible substrate sensor system to an external analysis device. In another embodiment, both an onboard analysis device and an external analysis device are used in combination.

In another embodiment, contacting the flexible substrate sensor system with the analyte can produce a detectable signal that correlates with the presence or activity of the analyte of interest.

In another embodiment, contacting the flexible substrate sensor system with the material can produce a detectable signal that correlates with the parameter of interest.

In another embodiment, the flexible substrate is a selected one of a sheet, strip, cylinder, coil or spiral, or other geometries.

In another embodiment, the connection can comprise a communication bus.

In another embodiment, the connection can comprise a programmable combiner.

In another embodiment, the connection can comprise a bus controller.

In another embodiment, the connection can comprise a wireless interface.

In another embodiment, the flexible substrate sensor system can comprise an onboard networking, communication and/or analysis component and/or system.

A method for detecting the presence or activity of an analyte (or parameter or characteristic) of interest in a fluid or solid is also provided. In one embodiment, the method can comprise the steps of providing a flexible substrate sensor system wherein the flexible substrate sensor system comprises a plurality of sensors, a flexible substrate, and a connection; contacting the analyte of interest with the flexible substrate sensor system, wherein the flexible substrate sensor system, when in contact with the analyte of interest, produces a detectable signal that correlates with the presence or activity of the analyte of interest; and correlating the detectable signal with the presence or activity of the analyte of interest. In one embodiment, the flexible substrate sensor system additionally comprises a network.

In another embodiment, the analyte of interest can be a biological organism or biologically derived product or contaminant such as cryptosporidium or *Giardia*, or a biomolecule such as a protein, ligand, steroid or other molecule that induces a biological effect.

In another embodiment, the analyte of interest can be an ion such as calcium or sodium, or a more complex molecule comprising an ion.

In another embodiment, the analyte of interest can be a heavy metal such as lead, or a poison such as cyanide or arsenic, or a more complex molecule comprising such components.

In another embodiment, the analyte of interest can be a metal salt or ion.

In another embodiment, the analyte of interest can be any compound (organic or inorganic) or any atom or ion known in the art, including, but not limited to, a trihalomethane, an organophosphate (for example, an organophosphate pesticide), and a toxic organic compound such as methyl tertiary-butyl ether (MBTE).

A method for detecting a parameter of interest in a fluid or in (or on) a solid is also provided. In one embodiment, the method can comprise the steps of providing a flexible substrate sensor system wherein the flexible substrate sensor system comprises a plurality of sensors, a flexible substrate and a connection; contacting the analyte, parameter or characteristic of interest with the flexible substrate sensor system, wherein the contacting of the analyte, parameter or characteristic of interest with the flexible substrate sensor system produces a detectable signal that correlates with the presence or activity of the parameter of interest; and correlating the detectable signal with the parameter of interest. In one embodiment, the flexible substrate sensor system additionally comprises a network.

In another embodiment, the parameter of interest can be any parameter of a fluid or solid commonly known in the art, such as pH, ionic strength, temperature, electrical impedance, turbidity, stress, strain, flexure, vibration or corrosion.

In another embodiment, the parameter of interest can be a structural or mechanical characteristic which may include, but is not limited to, stress, strain, flexure, vibration, non-vibratory motion, or acoustics.

In another embodiment, data exfiltration can be provided along with one or more communication buses arranged predominantly along the major axis of the substrate geometry.

In another embodiment, data exfiltration can be provided through two or more communication buses running along two or more axes of the substrate geometry.

In another embodiment, the data exfiltration network can automatically adjust to the dimensions of the substrate selected before or during deployment. As described below, a bus controller can be deployed in certain embodiments, so as to allow a local user to literally cut out a strip or sheet of the flexible substrate sensor system as needed, without having to re-design the communication network. In one embodiment, a bus controller can sense and automatically terminate an open circuit created when the substrate is cut or damaged (e.g., either intentionally or through normal use).

A method for monitoring the status (e.g., remaining power, sensitivity, availability) of one or more sensors in the plurality of sensors is also provided. In one embodiment, the one or more sensors in the plurality of sensors in the flexible substrate sensor system can be monitored continuously. In another embodiment, the one or more sensors can be monitored at selected intervals for selected times. In another embodiment, the one or more sensors can be monitored at intervals and for time periods determined by the history of the previous time periods, i.e. the sampling conditions are changed, using routine methods known in the art, and depending on whether an analyte was detected or on the value of the measurement of the analyte or parameter. In another embodiment, the one or more sensors in the flexible substrate sensor system can be monitored for functionality to determine whether a sensor is working correctly.

In one embodiment, the functional status of an individual or an array(s) of sensors can be communicated to an external device via the connection or networked with or without analysis by onboard system(s).

In another embodiment, the functional status of individual sensors or array(s) can be accessed and the measurements from non-functional sensors or array(s) of sensors are ignored by either onboard or external device(s) or system(s). Based on the analysis of this status, an entire flexible substrate sensor system could be replaced or individual sensors, or subsets or all of the sensors could be recalibrated.

BRIEF DESCRIPTION OF THE DRAWINGS

The present invention is described herein with reference to the accompanying drawings, in which similar reference characters denote similar elements throughout the several views. The figures are not necessarily drawn to scale. It is to be understood that in some instances, various aspects of the invention may be shown exaggerated or enlarged to facilitate an understanding of the invention.

DETAILED DESCRIPTION OF THE INVENTION

Figure 1:
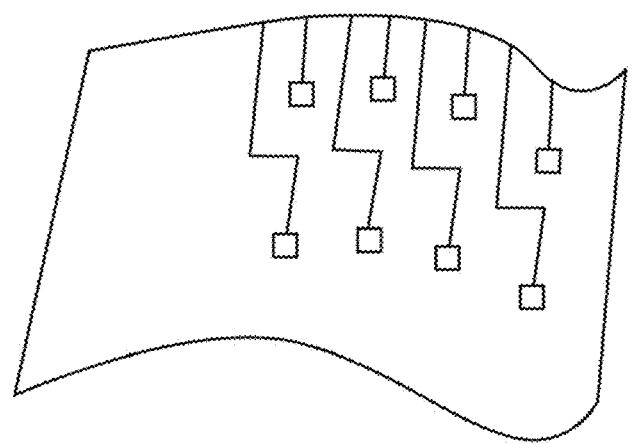
FIG. 1 shows an embodiment of the flexible substrate sensor system in which a plurality of sensors is situated on a flexible substrate.

An inexpensive sensor system utilizing flexible electronics for on-line real-time high-sensitivity sampling, monitoring, and analysis of a parameter (including a structural or mechanical characteristic) or analyte of interest in a fluid or in (or on) a solid is provided. The flexible substrate sensor system can be deployed in all types of systems that conduct, convey or distribute fluids or solids, including, but not limited to, distribution systems (for example, municipal water systems, oil or gas pipeline systems), industrial systems (such as production facilities, piping, and storage systems), large structures (such as dams, bridges, walkways, or buildings), and in any type of end-user system(s).

The flexible substrate sensor system of the invention can provide many advantages. It can be modular and inexpensive to manufacture. It can be shaped into a geometry that optimizes analyte or parameter detection for each analyte that is measured. It can use standard readout electronics that, in some embodiments, are located on-board and are networked to external devices. Maintenance of the flexible substrate sensor system can also be inexpensive. The analysis and communication subsystem(s) can monitor each sensor and/or sensor array, and can either relay their status to external devices or analyze it onboard. Decisions to replace the array(s) can be made externally or automatically. Due to their flexibility, the flexible substrate sensor systems can be replaced, which vastly extends the interval between maintenance and reducing maintenance costs. In some embodiments, the only maintenance required can be to periodically change the sensor array. The individual sensors employed in the system can have long lifetimes, can be resistant to biofouling and can monitor fouling. The flexible substrate sensor system can be easily adapted to analyte multiplexing, sampling of large volumes, and large scale multiplexing.

For clarity of disclosure, and not by way of limitation, the detailed description of the invention is divided into the subsections set forth below.

Sensors

The flexible substrate sensor system comprises a plurality of sensors or sensor groups that are located on a flexible substrate. The flexible substrate can assume various shapes and the sensor group can be configured in various patterns. For example, the sensor group can be distributed in an array either randomly or located in a set pattern, for example, one that optimizes volume sampling.

In one embodiment, the sensors in the plurality can be arranged in an array so that they measure a single analyte or parameter. In another embodiment, the sensors in the plurality can be arranged so that the overall array is divided into two or more subsets of sensors, with each subset measuring a different analyte or parameter. In another embodiment, sensors for different parameters or analytes can be interspersed among one another to form an array.

The number and arrangement of sensors in each subset can be varied, and the relative positions of sensors in each subset can also be varied. The juxtaposition of each of the subsets can also be varied. The subsets can also be separated from each other or intermixed.

The sensor group can be affixed, embedded in, linked or attached to the flexible substrate using any method known in the art. For example, the sensor can be attached by an adhesive, incorporated directly into the substrate, laminated with the substrate, deposited directly on the substrate, sandwiched between layers of the substrate, or encapsulated in the substrate or other material.

Any suitable sensor known in the art can be used. Examples of sensors suitable for use in the flexible substrate sensor system include chemical sensors, such as the Honeywell Durafet electrode (Honeywell International, Inc., Morristown, N.J.), which utilizes ISFET technology to measure pH. ISFETs are ion sensitive field effect transistors. These devices conduct more or less electrical current depending on the ion charge present at the gate of the device.

Other sensors suitable for use in the invention include temperature sensors, such as Resistance Temperature Devices (RTD) (e.g., from Omega Engineering, Inc., Stamford, Conn.). RTDs are well known in the art and capitalize on the fact that the electrical resistance of a material changes as its temperature changes. RTDs include metallic devices (commonly referred to as RTDs) and thermistors. As their name indicates, metallic RTDs rely on resistance change in a metal, with the resistance rising more or less linearly with temperature.

Other sensors suitable for use in the flexible substrate sensor system include pressure sensors, such as Honeywell silicon pressure sensors. These sensors (such as Honeywell 140PC series) are small, low cost, and reliable. They feature excellent repeatability, high accuracy, and reliability under varying environmental conditions. In addition, they feature highly consistent operating characteristics from one sensor to the next and interchangeability without recalibration. Pressure sensors known in the art generally contain sensing elements that consist of, e.g., four piezoresistors buried in the face of a thin, chemically-etched silicon diaphragm. A pressure change causes the diaphragm to flex, inducing a stress or strain in the diaphragm and the buried resistors. The resistor values change in proportion to the stress applied and produce an electrical output.

Sensors can also be fabricated using methods known in the art. For example, sensors can be fabricated using semiconductor fabrication methods including vapor deposition, laser annealing, lithographic patterning, sputtering, electroplating, or chemical deposition methods such as spin coating, spray coating, ink jet printing and related methods known in the art that produce thin film flexible structures with appropriate physical characteristics.

The flexible substrate sensor system is especially well suited for multiplexing. In certain embodiments, for example, the flexible substrate sensor system can comprise a plurality of sensors for each analyte, parameter or mechanical or structural characteristic (for example, pH, ionic strength, temperature, electrical impedance, turbidity). In other embodiments, the flexible substrate sensor system can comprise a plurality of sensors for each of a plurality of analytes, parameters or characteristics.

Flexible Substrate

The flexible substrate sensor system can comprise a flexible substrate, sensors and electronics that can assume various shapes and that can be configured in various patterns. The substrate can be made from several types of materials, including, but not limited to, various polymer materials, metals or glasses. The flexible sensors and electronics can be formed from various materials known in the art including, but not limited to, various metals, semiconductors, glasses and ceramics. For example, the flexible substrate can be formed into a shape that maximizes sensor contact with the sample to be analyzed for a parameter or analyte of interest.

One of the advantages of the flexible substrate sensor system is its flexibility with respect to shape. By exploiting different shapes, the sensor system can be adapted to many different facilities and environmental conditions, thereby enabling detection and monitoring at levels of sensitivity, speed, and safety that have not previously been possible. In one embodiment, the geometry of the system is configured using methods well known in the art to increase the surface area of the sensors and/or to decrease the flow impedance of the sensors.

With flexible substrates known in the art, various shapes are possible and the shape can be optimized for a desired application. For example, in one embodiment, the geometry of the flexible substrate bearing the sensors can be designed, using methods known in the art, to ensure mixing of the fluid comprising the analyte of interest or expressing the parameter of interest, thereby increasing exposure of the analyte or the fluid expressing the parameter of interest to the detector array. Shapes can include, but are not limited to, sheets, strips, cylinders, coils, and spirals. For example, sheets can be perforated to allow the passage of fluids. Vacuum sources or pumping capability can be incorporated to increase fluid flow across the substrate. Flow can be adjusted to enable laminar flow or turbulent flow to control fluid movement or mixing as needed using fins, protuberances or other topographical features.

One of the advantages of the flexible substrate sensor system is that it can measure a larger amount of a material (or of a system) than do other currently available sensor systems.

In one embodiment, the flexible substrate sensor system can make measurements from a large amount of a material or system being measured. In another embodiment, the amount of and the number and types of sensors can be so large that extremely large systems encompassing large areas (e.g. infrastructural facilities) or high fluid flow rates (e.g. gallons per hour to millions of gallons per hour) can be efficiently sampled for multiple analytes or parameters or combinations thereof over any appropriate range of sensitivity. For example, in certain embodiments of the invention, the number of sensors can be 2-10, 10-100, 100-1000, 1000-10,000, 10,000-1,000,000 or 1,000,000-100,000,000 sensors.

In another embodiment, a sheet of flexible substrate sensor arrays can be large, e.g., from several square feet to acres, enabling the measurement of much larger areas and/or volumes than is currently possible. The sheets deployed in waste containment facilities (see FIG. 2) can be several acres in areal dimensions.

In a specific embodiment, a flexible substrate sensor system can measure an analyte or a parameter of water in a water distribution system, be it a public or industrial system. According to this embodiment, any appropriate fraction or all of the water in a distribution system can be measured by a plurality of flexible substrate sensors on a sheet of flexible substrate.

Sheet Flexible Substrate

In another embodiment, the flexible substrate sensor system can comprise a flexible substrate that is a sheet. FIG. 1 shows an embodiment of the flexible substrate sensor system in which a plurality of sensors is situated on a sheet of flexible substrate.

Figure 2:
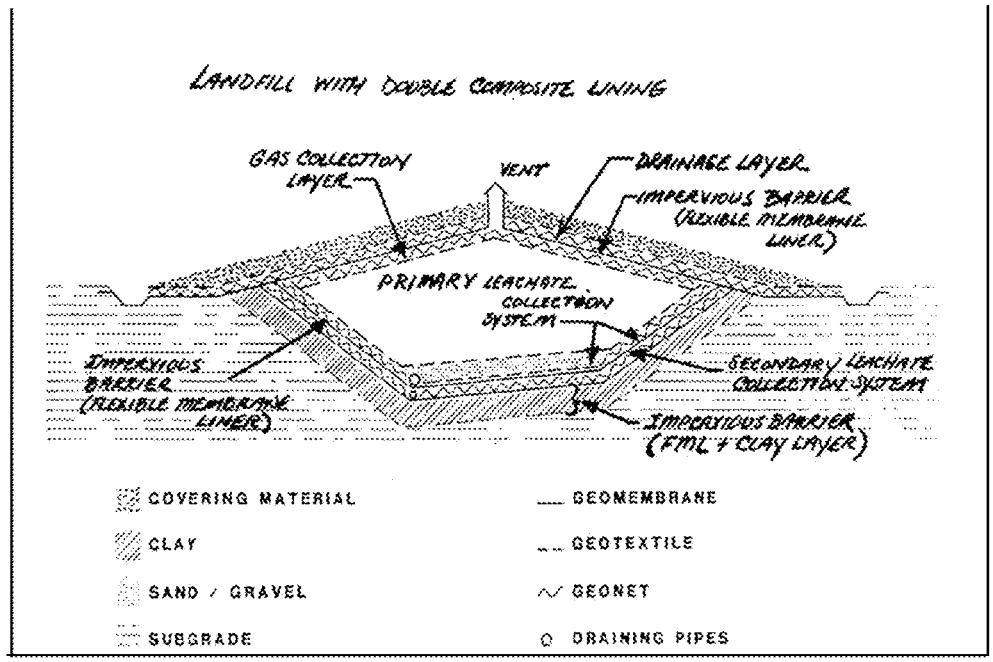
FIG. 2 shows a diagram of a landfill cross-section that illustrates the use of an embodiment of the flexible substrate sensor system in which the substrate is a sheet.

The sheet of substrate can be composed of any flexible substrate known in the art onto or within which one or more sensors can be located, for example, DuPont KAPTON® polyimide film (DuPont, Wilmington Del.). In one embodiment, the flexible substrate sensor system in sheet configuration can be deployed in a municipal or hazardous waste landfill. As illustrated in FIG. 2, such landfills are constructed with polymeric sheets that do not possess sensing capabilities. Various layers of the landfill, as shown in FIG. 2, are composed of sheets of geosynthetics (e.g., flexible membrane linings, woven or non-woven textiles, etc.) or horizons wherein sheets of geosynthetics are deployed. For example, the impervious barriers, drainage layers, leachate collection systems, and gas collection system all contain sheet-like structures onto which or within which a flexible substrate sensor system can be placed for use in chemical, biological, and/or structural/mechanical monitoring.

The flexible substrate sensor system of the invention can be integrated as one or more sheets that are incorporated in the lining of the landfill. The flexible substrate sensor system integrated in the lining can be located, for example, beneath the secondary leachate collection system, where it can detect quantity and type of contaminants that escape the primary lining system, or on the underside of the flexible membrane lining that caps the gas detection layer. A flexible substrate sensor system at this location can also be used to detect infiltration of water into the landfill.

The flexible substrate sensor system can be applied by methods known in the art, for example, by direct overlay on the underlying membrane of the secondary leachate collection layer or on the gravel or geonet in the gas detection layer. The flexible substrate of the sensor network can also be inserted as an integral, structural part of the landfill lining(s). In general, the flexible substrate can be applied in any location or orientation that allows the sensors and the fluid or solid containing an analyte of interest to come into contact with each other.

The flexible substrate sensor system of the invention can also be integrated into or applied to the lining system of chemical waste ponds and lagoons that are lined with flexible membranes and to layered drainage and substrate systems beneath road pavements, airport runways, leach fields, etc. The flexible substrate sensor system enables the layered system to become a sensing system with no compromise of its structural or drainage functionality.

Strip Flexible Substrate

Figure 3:
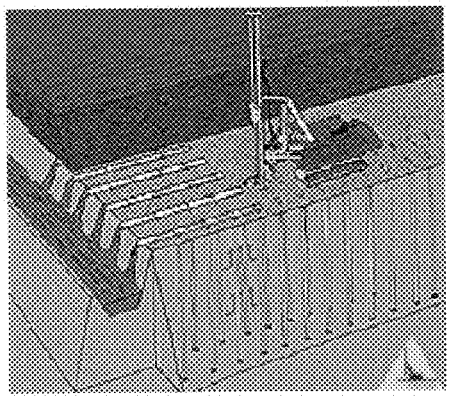
FIG. 3 shows a diagram of a wick drain installation.

In another embodiment, the flexible substrate sensor system can comprise a flexible substrate that is a strip. The strip can be oriented vertically, horizontally or inclined, or a plurality of strips can be arranged as a grid, or in a pattern. In one embodiment, the flexible substrate sensor system can be deployed in strips that are inserted, for example, in the ground, using equipment currently employed for the installation of wick drains (see, for example, services provided by American Wick Drain Corporation, Monroe, N.C., www.americanwick.com). As illustrated in FIG. 3, equipment that is known in the art and commercially available, such as mandrel insertion machinery, can be used to mechanically insert or push wick drains for drainage into the soil. In another embodiment the strips can be used to monitor plants in agricultural fields to optimize crop production. For example, they can be used to administer materials, such as water, fertilizer or pesticides as applicable, in response to external communication or a signal from an onboard system(s).

FIG. 3 shows a diagram of a wick drain installation (modified after American Wick Drain Corporation, Monroe, N.C., www.americanwick.com) illustrating the method of installation that can be used to place a flexible substrate sensor system in which the substrate is a strip enclosed by a geotextile. The wick drain is a flexible geotextile that, in certain embodiments, can be wrapped around a rectangular or elliptically shaped polymer core. The drain can be covered by and/or held within a heavy-duty steel mandrel and pushed to the desired depth, after which the mandrel can be withdrawn and the drain can be left in place.

Figure 4:
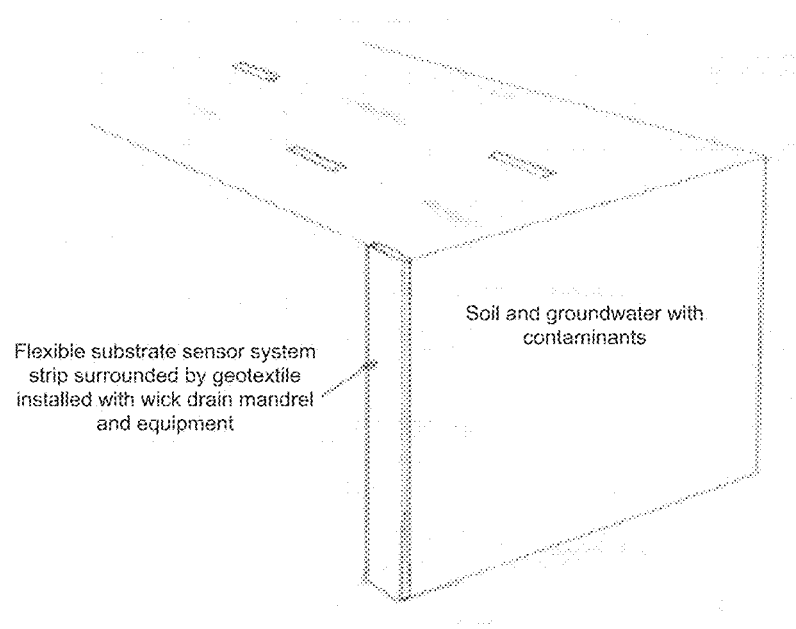
FIG. 4 shows a three-dimensional view of an embodiment of the flexible substrate sensor system in strip configuration. The arrow at left indicates the flexible electronics sensor network strip, surrounded by geotextile installed with wick drain mandrel and equipment, and contacting soil and/or groundwater with contaminants.

As shown in FIG. 4, the same process can be used to install a flexible substrate sensor system as a strip enclosed by a geotextile. FIG. 4 shows a three-dimensional view of another embodiment, a flexible substrate sensor system in strip configuration that can be installed, for example, in soil or groundwater that contains an analyte of interest, for example, a contaminant. In this embodiment, when a mandrel is used for insertion and then withdrawn, the sensor network strip can remain in communication with the groundwater through the permeable geotextile.

Figure 5:
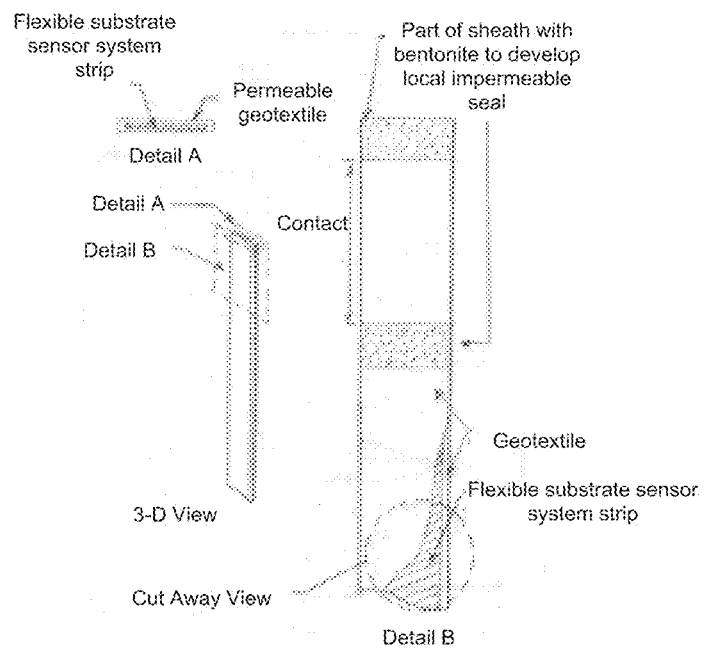
FIG. 5 shows a diagram of the details of the flexible substrate sensor system in strip configuration. Detail A shows a flexible substrate sensor system in strip configuration and permeable geotextile sheath. Detail B shows cross-sectional and cut-away views. The stippled sections indicated by arrows show part of the geotextile sheath embedded with bentonite to develop a local impermeable seal. The arrow designated "Contact" indicates a length where the flexible substrate sensor system in strip configuration is in contact directly with ground water through the permeable geotextile.

To provide for targeted monitoring of various subsurface horizons, the geotextile sheath can be fabricated with impervious sections, as illustrated in FIG. 5. FIG. 5 shows a diagram of the details of the flexible substrate sensor system in strip configuration that can be used, for example, for environmental monitoring of soil or groundwater. Impervious sections can be created using methods known in the art, for example, by embedding dry bentonite locally in the geotextile that expands and becomes impervious after contact with the groundwater. This action effectively seals the flexible substrate sensor system into discrete horizons for independent detection and evaluation of a contaminant "profile." The top part of the strip sensor, near the ground surface, can be sealed so that water cannot wick out of the system.

In contrast to a wick drain, this specific embodiment of the flexible, substrate strip sensor system does not promote drainage. Groundwater containing contaminants remain in place. In one embodiment, the flexible substrate strip sensor system can be sealed against vertical migration of contaminants up the strip and/or sealed at the surface. Such a system can replace environmental monitoring wells, which require very strict protective protocols to remove groundwater samples for chemical or biological analysis in off-site laboratories. According to this embodiment, the flexible substrate sensor system can monitor continuously and remotely in situ, and to a higher degree of sensitivity than do conventional systems, because it is not exposed to human intervention or contamination. Such an embodiment is much less expensive and safer than current methods for environmental monitoring of groundwater.

The flexible substrate strip sensor system can also be used for vertical control of drilling. Applications include, for example, oil well drilling and exploration for minerals. In this embodiment, the flexible substrate sensor system can additionally comprise accelerometers and inertial sensing devices.

Cylinder Flexible Substrate

Figure 6:
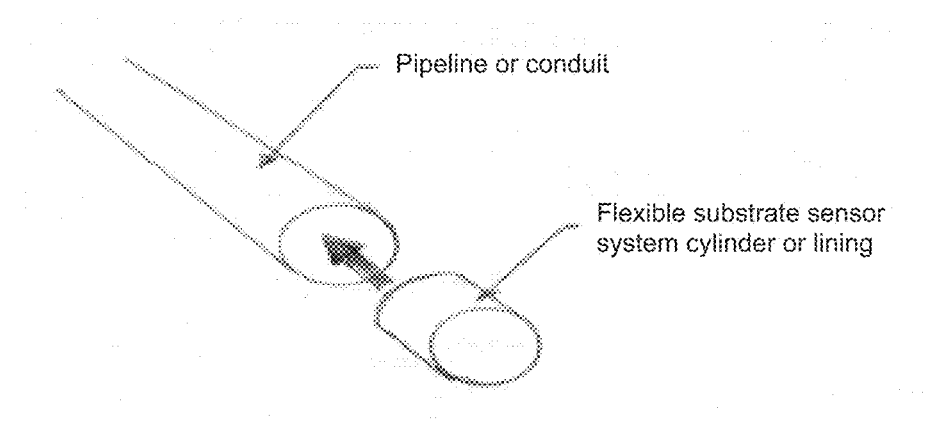
FIG. 6 shows a three-dimensional view of an embodiment of the flexible substrate sensor system in a cylindrical or liner configuration.

In another embodiment, the flexible substrate can be a cylinder. FIG. 6 shows a three-dimensional view of an embodiment of the flexible substrate sensor system in a cylindrical or liner configuration that can be introduced into (or applied as) a cylinder or lining to the interior of a new or existing pipeline, conduit, or duct, for example, in an oil, water or gas pipeline, or in an air duct.

The sensor system can monitor, for example, stress, strain, flexure, vibration, corrosion, chemicals, and/or biological media in fluid or solid environments. The flexible substrate sensor system in cylindrical or liner configuration can be installed in new pipelines and conduits during construction, or retrofitted into existing pipelines and conduits. Remote installation in existing pipelines and conduits can be accomplished using methods well known in the art. For example, tools well known in the art for insertion and expansion of cylindrical fixtures can be adapted, using routine methods, to install the flexible substrate sensor system. Inversion installation techniques well known in the art can also be used. See, for example, patents assigned to Insituform Technologies, Inc., Chesterfield, Mo. including U.S. Pat. No. 7,112,254 (Installation of cured in place liner with inner impermeable layer and apparatus), U.S. Pat. No. 7,108,456 (Steam cure of cured in place liner), U.S. Pat. No. 6,953,306 (Method of accurate trenchless installation of underground pipe), U.S. Pat. No. 6,932,116 (Fiber reinforced composite liner for lining an existing conduit and method of manufacture), U.S. Pat. No. 6,923,217 (Fiber reinforced composite liner for lining an existing conduit and method of manufacture), U.S. Pat. No. 6,899,832 (Installation of flexible lining with flexible collar for lining lateral pipelines), U.S. Pat. No. 6,708,728 (Installation of cured in place liners with air and steam and installation apparatus), U.S. Pat. No. 6,682,668 (Installation of cured in place liners with an endless reusable inflation bladder and installation apparatus), U.S. Pat. No. 6,679,293 (Pressurized bladder canister for installation of cured in place pipe), U.S. Pat. No. 6,612,340 (Turnback protection for installation of cured in place liners), U.S. Pat. No. 6,539,979 (Pressurized bladder canister for installation of cured in place pipe), U.S. Pat. No. 6,354,330 (Lining of pipelines with a flexible lining including a heat curable resin by curling in stages), U.S. Pat. No. 6,337,114 (Flexible lining with flexible collar for lining lateral pipelines), U.S. Pat. No. 6,146,491 (Lining of pipelines or passageways using a push rod adhered to rod and liner), U.S. Pat. No. 6,123,110 (Dual containment pipe system and a manhole system), U.S. Pat. No. 6,093,363 (Method of lining pipelines with flow-through apparatus and liner), U.S. Pat. No. 6,001,212 (Method for lining of lateral pipelines with flow-through apparatus), U.S. Pat. No. 5,975,878 (Apparatus for installation of lining with sealing collar), U.S. Pat. No. 5,942,183 (Method for everting a liner using a compact apparatus), U.S. Pat. No. 5,927,341 (Lining of "Tees" and "Wyes" in pipelines or passageways), U.S. Pat. No. 5,778,938 (Method of installation of dual containment pipe rehabilitation system), U.S. Pat. No. 5,743,299 (Dual containment pipe rehabilitation system and method of installation), U.S. Pat. No. 5,736,166 (Flow-through apparatus for lining of pipelines), U.S. Pat. No. 5,706,861 (Rehabilitation of pipelines and passageways with a flexible liner using an inflatible bladder), U.S. Pat. No. 5,624,629 (Installation of lateral linings with sealing collar from the main pipeline out), U.S. Pat. No. 5,597,353 (Compact apparatus for everting a liner and method), U.S. Pat. No. 5,577,864 (Apparatus relating to the linings of pipelines and passageways), U.S. Pat. No. 5,546,992 (Dual containment pipe rehabilitation system), U.S. Pat. No. 5,510,078 (Method of lining pipelines and passageways), U.S. Pat. No. 5,409,561 (Lining of passageways), U.S. Pat. No. 5,407,630 (Lining of pipelines or passageways), U.S. Pat. No. 5,393,481 (Lining of pipelines or passageways), U.S. Pat. No. 5,384,086 (Lining of pipelines or passageways), U.S. Pat. No. 5,374,174 (Apparatus for/installing a liner within a service pipe or the like), U.S. Pat. No. 5,318,395 (Method and apparatus for porting lateral connections in lined pipelines), U.S. Pat. No. 5,285,741 (Method of producing a flexible tubular lining), U.S. Pat. No. 5,172,730 (Two-wall leakage detection system for a pipe), U.S. Pat. No. 4,980,116 (Lining of pipelines and passageways), U.S. Pat. No. 4,836,715 (Passageway lining material), U.S. Pat. No. 4,778,553 (Method of lining a pipeline with a flexible tubular sleeve), U.S. Pat. No. 4,758,454 (Lining of passageways), U.S. Pat. No. 4,680,066 (Lining of pipelines or passageways), U.S. Pat. No. 4,677,472 (Apparatus for inspecting the interior of a pipeline), U.S. Pat. No. 4,637,754 (Lining of pipelines and passageways), U.S. Pat. No. 4,622,196 (Lining of pipelines and passageways), U.S. Pat. No. 4,581,247 (Lining of pipelines and passageways), U.S. Pat. No. 4,581,085 (Lining of pipelines or passageways), U.S. Pat. No. 4,577,388 (Method of cutting apertures in lining in underground pipes), U.S. Pat. No. 4,439,469 (Formation of a lining in pipelines), U.S. Pat. No. 4,434,115 (Method for remote lining of side connections), U.S. Pat. No. 4,401,696 (Lining of pipelines and passageways), U.S. Pat. No. 4,385,885 (Lining of passageways), U.S. Pat. No. 4,064,211 (Lining of passageways), and U.S. Pat. No. 4,048,512 (System for generating power from wave motions of the sea).

Coil or Spiral Flexible Substrate

In another embodiment, the flexible substrate can be a coil or spiral. In a specific embodiment, the axis of the spiral or coil can be parallel to the direction of fluid flow. This allows large volume of fluids to be monitored without sacrificing detection sensitivity and specificity. For example, the flexible substrate can be a spiral or coil whose axis is parallel with that of a pipe through which water is flowing, i.e. the water flows along the surface of the substrate. The spiral or coil flexible substrate sensor system can be located, for example, in a side stream parallel to a larger distribution line.

Figure 7:
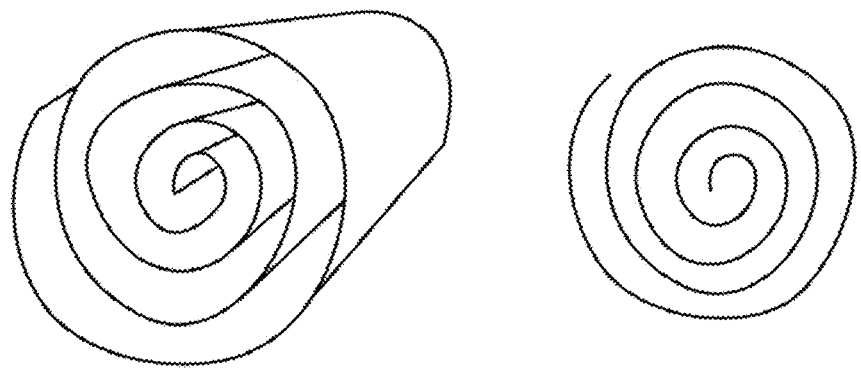
FIG. 7 shows an embodiment of the flexible substrate sensor system in which a sheet of sensors arrays is formed into a spiral such that a fluid flows between the layers.

In the embodiment shown in FIG. 7, a sensor array on a sheet of flexible substrate is rolled into a spiral and mounted in the water system such that the axis of the spiral is parallel to the axis of the pipe and such that water flows between the layers of the spiral. Fluid can flows between the layers, bringing a large volume of the material being measured in contact with the individual sensors. The fluid flow in this embodiment is parallel to the axis of the spiral. The flexibility of the sensor/substrate system allows the sensor array to conform to the geometry of the system to optimize the measurements. According to this embodiment, a solid can also be measured.

Figure 8:
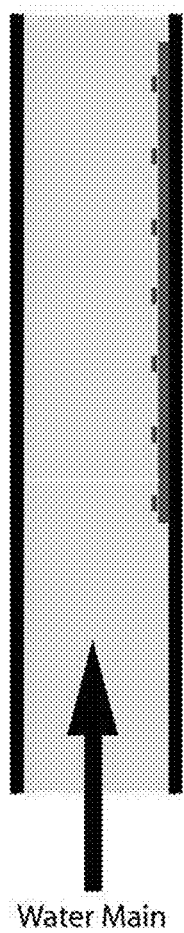
FIG. 8 shows an embodiment of the flexible substrate sensor system in which an array of sensors is wrapped around the inside of a cylinder, such as a pipe or duct, to sense the chemical or biological content of the fluid as well as the physical characteristics of the fluid (e.g., flow rate, pressure, etc.) flowing therein such as in a water main.

FIG. 8 shows an embodiment of a flexible substrate sensor system in which an array of sensors is wrapped around the inside of a cylinder, such as a pipe, to sense the fluid flowing in the pipe. The cylinder can also be a structural member of a larger structure that is being monitored, for example, for stress or vibration.

Figure 9:
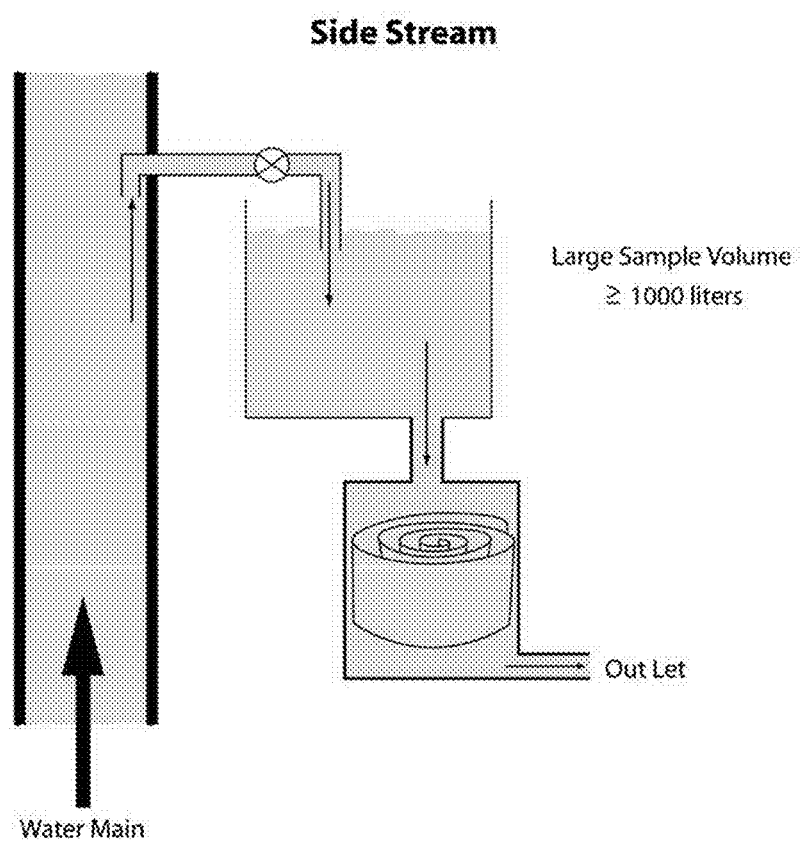
FIG. 9 shows an embodiment of the flexible substrate sensor system in which a spiral sensor array analyzes or measures a fluid system, and in which the main flow is sampled by a side stream arrangement such as in a water distribution system.

FIG. 9 shows an embodiment of the flexible substrate sensor system comprising a spiral sensor array for measurement of a fluid system, for example, a water system in which the main flow is sampled by a side stream arrangement. According to this embodiment, the spiral array can be mounted as a side stream arrangement or directly in the main flow.

External Connections, Data Extraction and Data Transmission

A flexible substrate sensor system is provided that can rapidly and effectively transfer information from one or more sensors to an onboard and/or an external device for analysis and reporting of the sensor measurements. The invention also provides networking technology for efficient data extraction and data integrity. In one embodiment, the sensors are connected to the outside by physical contacts or connectors or by wireless networks that utilize a plurality of frequencies and power levels suitable for short or long-distance communication. Physical contacts or connectors suitable for use in the invention are well-known in the art, for example, using direct electrical wiring, using conversion of data from electrical to optical followed by communication as optical data using fiber optic systems and reconversion of the signals to electrical signals. The claimed system also supports the use of free-space optical, wireless, and surface acoustic wave communication across and through the substrate.

In one embodiment, a local cluster of sensors is coupled to the communication bus through a two-step interface comprising a programmable combining stage and a bus controller. The sensors in the local cluster are coupled to a programmable combiner, allowing for varying levels of local data aggregation or fusion on the substrate. By varying the degree of aggregation or fusion, the probability of false detection and missed detection can be tailored to suit the application. One approach is to use a voting protocol, described in more detail hereinbelow. Other well known techniques for improving accuracy can also be used.

Data buses may be arranged along one or more dimensions of the substrate as dictated by the substrate geometry. In one embodiment, the dimensions of a sheet of sensors may be selected during deployment. Bus controllers arranged along a rectangular grid of buses sense open connections created when the sheet is cut to size, terminating the communication buses and adjusting the bus communication protocol as appropriate.

Any suitable method known in the art for data extraction or transmission can be used. The data can be sent in raw form (or "as is"), in compressed form (for example using any convenient compression algorithm such as LZ-77, LZ-78, LZW), in encrypted form using any symmetric or asymmetric key cryptosystem, such as triple-DES or RSA, or using audio encoding (such as MPEG audio encoding) and a look up table for transmitting signals that can be immediately presented to a user in a form understandable to any operator (for example, messages such as "There is a serious fault at station 23. Send an inspection team.", or "There is a breach in the pipeline.", or "Fire emergency.") In general, the claimed system supports the use of signal code books that have been optimized for compression and/or human intelligibility as dictated by the intended application.

In one embodiment, the flexible substrate sensor system comprises a communication bus. In another embodiment, the output of a combiner is coupled to a bus controller, which provides access to the communication bus. In another embodiment, the communication bus is an asynchronous carrier sense multiple access bus. In another embodiment, a synchronous slotted approach is adapted, according to the requirements of the application, using methods well known in the art. For example, one can use any of time division multiplexing (TDM), polling, or interrupt-driven communication systems. Polling signals can be provided through wired or wireless means from local controllers, as well as global controllers external to the substrate, such as handheld RFID readers and remote ground-based or airborne data acquisition vehicles.

In certain embodiments, the communication bus can comprise one or more conductive paths interconnected so as to provide fault tolerance and system reliability. For example, buses may be deployed in parallel, with interconnections included to insure end-to-end connectivity in the event of a failure in some portion of one of the buses. Buses may also be deployed in two dimensional patterns, such as a grid, that supports multiple routes between one or more sensor clusters and the output point or points of the substrate.

The local sensor cluster, combiner, and bus interface can be, in certain embodiments, replicated one or more times along one or more axes of the substrate. The flexible substrate comprised in the flexible substrate sensor system can create a networking problem, which can occur if the structure is long, and if the system contains many sensors. The networking problem can be solved through the use of variable local aggregation/data fusion and one or more communication buses that exploit the topology of the sensing system. For example, in one embodiment, the communication bus(es) runs the entire length of the major axis of the substrate. In another embodiment, the communication bus(es) runs through a portion of the length of the major axis of the substrate. Data rates along the bus or buses are varied by varying the level of local data aggregation and/or fusion. For example, a local cluster of sensors may only transmit a single piece of information which is representative of information or data taken from individual sensors in the cluster that has been aggregated and/or fused; when compared to data management schemes which allow all or some portion of sensors in the cluster to independently use a bus or several buses to pass data to an output point, this aggregated data management and communication approach results in an overall reduction in data transmissions and use of sensor system resources.

Wireless Interface

In one embodiment, the combiner is coupled to a wireless (for example, radio or infrared) interface that allows for over-the-air programming of the combiner. The flexible substrate sensor system can thus be reprogrammed in situ. This allows, for example, multistage detection schemes. The wireless interface can implement any interface known in the art, for example, wireless LAN technology, such as Bluetooth, any version of 802.11 or 802.15, and wireless telephony. Such a design allows all wireless interfaces on the substrate to share a common wireless communication medium.

In another embodiment, the wired interface system or the wireless interface is also used as a means for sensor testing and maintenance. According to this embodiment, the wired interface and/or wireless interface provides a means for implementing sensor sleep or cleaning cycles, thus increasing the lifetime of the flexible substrate sensor system.

In another embodiment, the wireless interface is also used to control the deployment of a sheet of sensor arrays to bring a new or an additional set of sensors into contact with the fluid or solid being analyzed.

The flexible substrate sensor system also provides dimensional stability, allowing precision measurements of a number of readout technologies, including but not limited to electrical and optical readouts. The long-term stability of the flexible substrate sensor system in a fluid or solid system, i.e. infrequent change out, is also of great benefit, especially when combined with the potential to render the bulk of the surface immune to fouling, especially biofouling. Change-out-time can be further extended by mounting a roll of arrays, analogous to a roll of paper towels, such that a new array of sensors is rolled into position to replace a saturated or damaged array. This can be done under external network control. Further, the detection electronics and electronic information handling can also be fabricated on the flexible substrate and can also be electronically multiplexed to minimize operational energy consumption while optimizing computational and communication efficiencies. On-substrate electronics can be optimized for remote communication, for example, by radio-frequency or infrared interfaces. Thus a centralized site can monitor a plurality of sensor installations distributed over any geographical area.

The flexible substrate sensor system of the invention therefore provides an inexpensive rapid response system for long-term precision monitoring of any type of fluid or solid system on any scale or at any point in the system for a plurality of physical parameters and/or chemical or biological analytes.

The invention is intended to detect multiple chemical, biological, and physical characteristics of fluids and/or solids in any environment. In one embodiment, the analyte or parameter is associated with a fluid. In another embodiment the analyte or parameter is associated with a fluid in the form of a gas or in air. The analyte of interest can occur naturally or can be intentionally or unintentionally added. The parameter of interest can also occur naturally, or can be intentionally or unintentionally induced.

Examples include but are not limited to water quality monitoring in distribution pipelines or containers receiving water from distribution pipelines; detection of contaminants in fluids, for example, fluids in or derived from municipal solid waste landfills, buried waste storage areas, or hazardous waste landfills; municipal water or groundwater monitoring for contaminants; detection of metal ions such as sodium or calcium in clean rooms used for electronic fabrication; detection of air-borne biological or chemical constituents; monitoring of pressure, force or leakage in pipelines or conduits; and monitoring orientation, force, or a subsurface chemical constituent, for example, in the drilling or exploration activities associated with oil well and mining development. As an example, the flexible substrate sensor system can be used to monitor municipal potable water systems (or municipal sewage clean-up systems) to protect against the inappropriate introduction (or inappropriate release) of unwanted substances in the water.

The flexible substrate sensor system provided by the invention can be used to detect an analyte or parameter of interest in any fluid or solid at any point in the distribution or end-use system being analyzed. The sensor array can be deployed in almost any geometric configuration, thus making it possible to sample large volumes or even the entire volume of a fluid or solid at high sensitivity for any number of analytes or parameters. The array can be multiplexed with respect to the number of sensors detecting a specific analyte or parameter, the number of analytes or parameters being detected, and the transfer of information to onboard and external devices. The combination of the number of sensors and the geometric configuration allows any volume of fluid to be sampled at high sensitivity. The geometric configuration also allows the flexible substrate sensor system to be deployed without significantly increasing the impedance of fluid flow and in some case will not have any effect on the impedance.

According to the invention, the flexible substrate sensor system is highly stable and long-lived, requiring infrequent change-out. In one embodiment, a plurality of sensor arrays or a plurality of flexible substrate sensor systems is mounted at the same time such that only one is in use but others can be indexed into place as needed, for example, if a working system is saturated or damaged. This enables change-out of the system to be even less frequent.

The invention also provides the ability to monitor the status (e.g., remaining power, sensitivity, availability) of one or more sensors. In one embodiment, the one or more sensors in the flexible substrate sensor system are monitored continuously. In another embodiment, the one or more sensors are monitored at selected intervals for selected times. In another embodiment, the one or more sensors are monitored at intervals and for time periods determined by the history of the previous time periods, i.e. the sampling conditions are changed, using routine methods known in the art, depending on whether an analyte was detected or on the value of the measurement of the analyte or parameter. In another embodiment, the one or more sensors in the flexible substrate sensor system are monitored for functionality to determine whether a sensor is working correctly.

In another embodiment, the one or more sensors in the flexible substrate sensor system are monitored for functionality to determine whether a sensor is working correctly. For example, if a sensor is determined to be damaged or operating sporadically, or saturated, future measurements from that sensor can be ignored or eliminated. If a measurement for an analyte or parameter of interest was below some cut-off value, a sensor or plurality of sensors can be shut down or sampled at longer time intervals, or a subset of the sensors can be measured to save power. For example, if the measurement increased, the number of active sensors can be readjusted.

In one embodiment, the sensor system of the invention comprises a network that controls the readout of the sensor array as well as optimizes the array's operation and life-time.

In another embodiment, the network initiates one or more operations. In another embodiment, the network initiates sensor cleaning or sleep cycles. In another embodiment, the network changes readout sequences to optimize detection of an analyte or parameter (or subset thereof) of interest. In yet another embodiment, the network also indexes the sensor group to expose a new working sensor group to the fluid expressing the analyte or parameter of interest, in response to a preprogrammed set of circumstances or measurements, or to external data or commands. These operations initiated by the network can be in response to sensor measurements or the input of external data.

Analysis Device

The flexible substrate sensor system can be connected to an onboard or external analysis device. For example, the system may be connected to an impedance spectrometer, which measures AC and DC resistance, capacitance and inductance. In some embodiments, the analysis device comprises a programmable general computer with suitable analysis software that can operate thereon to perform analyses, and additionally comprising, as may be required, hardware configured to inter-convert analog and digital signals.

Powering the Flexible Substrate Sensor System

The flexible substrate sensor system can be equipped with micro-mechanical devices to harness the energy from fluid flow in a pipeline, conduit, or duct to power the sensors and the transmission of data to receiving stations. Examples of micro-mechanical devices that can develop electrical energy from gas or water flow include micro-turbines and piezoelectric generators. A micro-turbine converts water or gas flow into electricity by means of water flow across a micro-turbine rotor that turns a micro-generator, thus producing electric power to energize the sensor system. Micro-turbine rotor diameters as small as 4 mm have been successfully demonstrated in working devices (Peirs, J., D. Reynaerts, and F. Verplaetsen, 2004, *A Microturbine for Electric Power Generation*, Sensors and Actuators, Elsevier, A 113, 86-930.) In addition, local turbulence in water and gas flow can be used to generate vibration in piezoelectric crystal structures that convert vibration to electric current. The piezoelectric material can be fabricated, for example, by depositing lead zirconate titanate onto silicon. Through cantilever motion under locally turbulent fluid flow, for example, the piezoelectric material will generate electric current.

In alternative embodiments, the flexible substrate sensor system can be powered by a central power supply, by locally generated power, for example, using alternative energy sources such as photovoltaics, or by local power storage devices such as batteries or uninterruptible power supplies (UPS).

The following examples are offered by way of illustration and not by way of limitation.

EXAMPLES

Example 1

Sensor System for Collaborative Sensing

The sensor system of the invention comprises a flexible substrate, which, in certain embodiments, could possibly pose a collaborative sensing problem and a communication networking problem. Both these problems are solved in the example described below.

The collaborative sensing problem lies in the use of large numbers of sensors to detect and/or measure the presence of target materials in a sensed medium. Each sensor will have an associated probability of detection (i.e., the likelihood that the sensor will detect the presence of a target analyte when the target is present) and a probability of false alarm (i.e., the likelihood that the sensor will report the presence of the target when it is not actually present). Data fusion is generally the process of collecting, associating, and merging data from multiple sensors. By fusing data from multiple sensors, the probability of accurate detection can be increased, while the probability of false alarm is reduced. Voting provides a simple example of a sensor data fusion technique, though those of skill in the art will recognize that there are many other possibilities.

Figure 10:
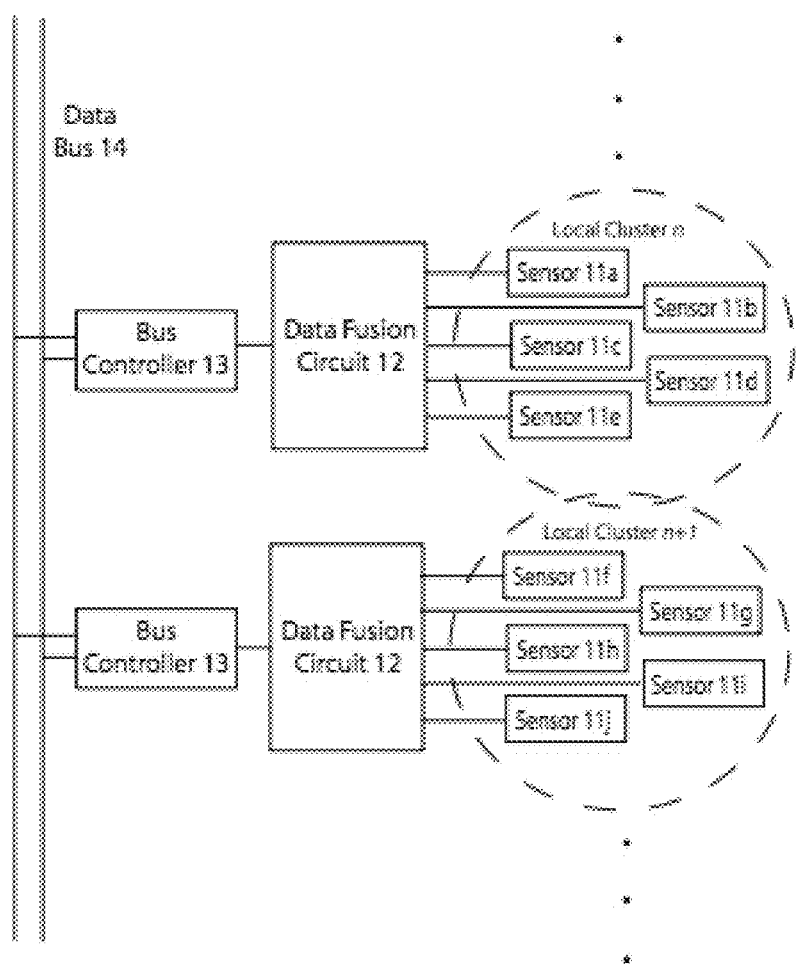
FIG. 10 shows a diagram of the embodiment of the flexible substrate sensor system described in Example 1, comprising Sensors (11$a$-$j$), Data fusion circuit (12), Bus controller (13), and Data bus (14). Dashed lines encircle Local Cluster n and Local Cluster n+1.

In this example, the sensor system of the invention comprises sensors that are arranged into local clusters, as shown in FIG. 10. Sensors 11a, 11b, 11c, 11d, and 11e form a single cluster n. The sensors in a cluster are coupled to a data fusion circuit 12. In this embodiment, the sensors are coupled individually to the data fusion circuit, though in other embodiments, the sensors are coupled in pairs or in an arrangement involving a plurality of sensors.

The data fusion circuit 12 can be a simple voting circuit. In a preferred embodiment it is a programmable combiner capable of implementing a wide variety of data fusion or data aggregation algorithms. By varying the degree of aggregation or fusion, the probability of false detection and missed detection can be tailored to suit the application, using methods known in the art. In addition, multi-stage detection algorithms, for example, can be implemented in which additional tests can be performed after an initial detection event.

The data networking problem is created by the potential array of geometries that can be assumed by the claimed sensing system. One solution lies in the deployment of one or more communication buses that exploit the topology of the sensing system; for example, buses running the length of the major axis of the substrate can be used.

In the embodiment depicted in FIG. 10, the output of the data fusion circuit 12 in each local cluster is coupled to a bus controller 13, which provides access to the communication bus 14. The communication bus can be implemented as an asynchronous carrier sense multiple access bus, or a synchronous slotted approach can be adopted as needed by the application. The communication bus can comprise of one or more conductive paths interconnected so as to provide fault tolerance and system reliability. The local sensor cluster, data fusion circuit, and bus controller are replicated repeatedly along the major axis of the substrate.

In another embodiment, the data fusion circuits are coupled to a radio interface that allows for over-the-air programming. The proposed sensing system can thus be reprogrammed in situ. This will allow, for example, multistage detection schemes. The radio interface can implement wireless LAN technology, such as Bluetooth, 802.11 or 802.15, allowing all radio interfaces on the substrate to share a common wireless communication medium.

The radio interface can also be used as a means for sensor testing and maintenance. It can, for example, provide a means for implementing sensor sleep or cleaning cycles, thus increasing the lifetime of the sensing system. It can also control the deployment of a large sheet of sensor arrays to bring a new set of sensors into contact with the fluid.

In some embodiments, a combination of wired and wireless communication systems can be used.

Example 2

Use of Flexible Substrate Sensor System in a Municipal or Industrial Water System This example describes the use of a flexible substrate sensor system in a municipal or industrial water system.

An array of sensors for a select number of parameter and analytes is multiplexed to optimize sampling of a large volume while maintaining high sensitivity, using methods well known in the art. Such parameters and analytes include, but are not limited to temperature, pH, ionic strength, turbidity, electrical impedance, biological contaminants such as cryptosporidium or *Giardia*, ions such as calcium or sodium, heavy metals such as lead, poisons such as cyanide, arsenic, and organic compounds such as trihalomethanes, organophosphates (for example, organophosphate pesticide), and MTBE.

A plurality of sensors can be provided for each parameter or analyte, and distributed in the sensor group or array, either randomly or in a set pattern that optimizes volume sampling. The sensors for all the parameter/analytes are interspersed among each other to form an array. The array of sensors is disposed on a flexible substrate with interconnections to the outside via physical contacts or by a wireless network. In one embodiment, the flexible substrate is formed into a geometry that maximizes sensor contact with the water. Various geometries can be used.

The first geometry is a spiral such as a helix whose axis is parallel with that of a pipe through which the water is flowing, i.e. the water flows along the surface of the substrate. The spiral sensor array can be located in a side stream parallel to a larger distribution line. Depending on the system, and the location of the flexible substrate sensor system in the water system, a variety of pressure and check valves can also be employed to control flows to and from the flexible substrate sensor system. The flexible substrate sensor system can be mounted in a section of a side stream. The example shown in FIG. 9 is for an open tank side stream. The flexible substrate sensor system array can also be implemented in a closed pipe with the side stream water either being pumped back into the distribution pipe or directed to waste. A connector to the outside of the side stream pipe allows electronic devices to monitor the response of each sensor, using, for example, a multiplexed network type sampling method known in the art. Another embodiment of the flexible substrate sensor system incorporates detection and, optionally, multiplexing electronics on the flexible substrate.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

What is claimed is:

1. A flexible substrate sensor system for detecting a parameter, analyte or characteristic of interest in a large volume of fluid or in or on a large volume solid comprising:
   a. a plurality of sensors;
   b. a flexible substrate;
   c. an onboard network on the substrate; and
   d. a connection between the sensors and the onboard network,
   wherein:
   the onboard network reads out the sensors or collects information from the sensors,
   the plurality of sensors is optimized for volume sampling or sampling the surface of the volume,
   the optimization of the plurality of sensors comprises conforming the plurality to a specific geometry of a measurement environment or condition of interest, the plurality of sensors is embedded, incorporated or encapsulated in or on the flexible substrate,
   the connection comprises a communication bus On the substrate, and
   the connection comprises a bus controller,
   wherein the bus controller senses and automatically terminates an open circuit in the flexible substrate.

2. The flexible substrate sensor system of claim 1 wherein the analyte of interest is a fluid or a solid.

3. The flexible substrate sensor system of claim 1 wherein:
   a. the plurality of sensors is arranged on the flexible substrate to form at least one measurement array; and
   b. each sensor of the plurality of sensors forming the measurement array performs a measurement of the parameter, analyte or characteristic of interest that is independent of the other sensors of the plurality of sensors forming the measurement array.

4. The flexible substrate sensor system of claim 1 wherein at least one sensor of the plurality of sensors is networked to at least one other sensor.

5. The flexible substrate sensor system of claim 1 wherein:
   a. the plurality of sensors detects at least two analytes, parameters, or characteristics of interest (or a combination thereof), and
   b. the plurality of sensors is disposed on the flexible substrate in a multiplex measurement array.

6. The flexible substrate sensor system of claim 1 wherein the connection is operably connected to an onboard analysis device.

7. The flexible substrate sensor system of claim 1 wherein the connection is operably connected to an external analysis device.

8. The flexible substrate sensor system of claim 1 wherein contacting the flexible substrate sensor system with the analyte, parameters, or characteristic of interest produces a detectable signal that correlates with presence or activity of the analyte, parameter, or characteristic of interest.

9. The flexible substrate sensor system of claim 1 wherein the flexible substrate is a selected one of a sheet, strip, cylinder, coil or spiral.

10. The flexible substrate sensor system of claim 1 wherein the connection comprises a programmable combiner.

11. The flexible substrate sensor system of claim 1 wherein the connection comprises a wireless interface.

12. The flexible substrate sensor system of claim 1 wherein:
   a. the flexible substrate is a sheet, and
   b. the plurality of sensors is disposed on the sheet to form at least one measurement array.

13. The flexible substrate sensor system of claim 12 comprising a plurality of measurement arrays, wherein:
   a. each measurement array of the plurality is disposed on the sheet so that the measurement array is capable of being exposed to the parameter, analyte or characteristic of interest, and
   b. at least one exposed measurement array is replaced by translocating the sheet so as to expose an unexposed measurement array to the parameter, analyte or characteristic of interest.

14. The flexible substrate sensor system of claim 1, wherein the degree of local data aggregation or fusion performed on the substrate by the onboard network is varied.

15. The flexible substrate sensor system of claim 14, wherein the degree of local data aggregation or fusion performed on the substrate by the onboard network is varied to:
   (a) tailor the probability of false detection and missed detection, or
   (b) vary data rates along the communication bus or communication buses.

16. The flexible substrate sensor system of claim 1 wherein a computation regarding a parameter, analyte or characteristic of interest is performed onboard.

17. The flexible substrate sensor system of claim 16 wherein the onboard computation is performed after or before networking.

18. A method for detecting an analyte, parameter or characteristic of interest in a large volume of fluid or in or on a large volume solid, comprising the steps of:
   a. providing a flexible substrate sensor system wherein the flexible substrate sensor system comprises a plurality of sensors, a flexible substrate, an onboard network on the substrate and a connection between the sensors and the network, wherein:
      the onboard network reads out the sensors or collects information from the sensors,
      the plurality of sensors is optimized for volume sampling,
      the optimization of the plurality of sensors comprises conforming the plurality to a specific geometry of a measurement environment or condition of interest,
      the plurality of sensors is embedded, incorporated or encapsulated in or on the flexible substrate, and
      the connection comprises a communication bus on the substrate;
   b. contacting the analyte, parameter or characteristic of interest with the flexible substrate sensor system, wherein the contacting of the analyte, parameter or characteristic of interest with the flexible substrate sensor system produces a detectable signal that correlates with the presence or activity of the analyte, parameter or characteristic of interest;
   c. correlating the detectable signal with the analyte, parameter or characteristic of interest; and
   d. providing data exfiltration, wherein the data exfiltration network automatically adjusts to a dimension of the flexible substrate selected before or during deployment.

19. The method of claim 18 wherein the data exfiltration is provided by at least one communication bus arranged predominantly along the major axis of the substrate geometry.

20. The method of claim 18 wherein the data exfiltration is provided through at least two communication buses running along at last two axes of the substrate geometry.

21. A method for detecting an analyte, parameter or characteristic of interest in a large volume of fluid or in or on a large volume solid, comprising the steps of:
   a. providing a flexible substrate sensor system wherein the flexible substrate sensor system comprises a plurality of sensors, a flexible substrate, an onboard network on the substrate and a connection between the sensors and the network, wherein:
      the onboard network reads out the sensors or collects information from the sensors,
      the plurality of sensors is optimized for volume sampling,
      the optimization of the plurality of sensors comprises conforming the plurality to a specific geometry of a measurement environment or condition of interest,
      the plurality of sensors is embedded, incorporated or encapsulated in or on the flexible substrate, and
      the connection comprises a communication bus on the substrate;
   b. contacting the analyte, parameter or characteristic of interest with the flexible substrate sensor system, wherein the contacting of the analyte, parameter or characteristic of interest with the flexible substrate sensor system produces a detectable signal that correlates with the presence or activity of the analyte, parameter or characteristic of interest; and
   c. correlating the detectable signal with the analyte, parameter or characteristic of interest,
wherein the flexible substrate sensor system additionally comprises a bus controller, wherein the bus controller senses and automatically terminates an open circuit in the flexible substrate.

22. The method of claim 21 additionally comprising monitoring status of a sensor in the plurality of sensors.

23. The method of claim 22 wherein the status is selected from the group consisting of remaining power of the sensor, sensitivity of the sensor and availability of the sensor.

24. The method of claim 22 wherein the monitoring of the status of the sensor in the plurality of sensors is continuous monitoring.

25. The method of claim 22 wherein the monitoring of the status of the sensor in the plurality of sensors is interval monitoring.

26. The method of claim 22 wherein the monitoring of the status of the sensor in the plurality of sensors is functionality monitoring.

27. The method of claim 18 or 21 wherein the analyte, parameter or characteristic of interest is selected from the group consisting of a biological organism, a biologically derived product, a biologically derived contaminant and a biomolecule.

28. The method of claim 18 or 21 wherein the analyte, parameter or characteristic of interest is an ion or a complex molecule comprising an ion.

29. The method of claim 18 or 21 wherein the analyte, parameter or characteristic of interest is a heavy metal, a derivative of a heavy metal or a complex molecule comprising a heavy metal.

30. The method of claim 18 or 21 wherein the analyte, parameter or characteristic of interest is an organic compound.

31. The method of claim 18 or 21 wherein the analyte, parameter or characteristic of interest is selected from the group consisting of pH, ionic strength, temperature, electrical impedance, turbidity, stress, strain, flexure, vibration, non-vibratory motion, acoustics and corrosion.

32. The method of claim 18 or 21 wherein the onboard network performs local data aggregation or fusion on the substrate.

33. The method of claim 32, further comprising the step of varying the degree of local data aggregation or fusion performed on the substrate by the onboard network.

34. The method of claim 33 wherein the degree of local data aggregation or fusion performed on the substrate by the onboard network is varied to:
   (a) tailor the probability of false detection and missed detection, or
   (b) vary data rates along the communication bus or communication buses.

35. The method of claim 18 or 21 wherein a computation regarding a parameter, analyte or characteristic of interest is performed onboard.

36. The method of claim 35 wherein the onboard computation is performed after or before networking.

37. The method of claim 18 or 21 wherein the onboard network performs local data aggregation or fusion on the substrate.

38. The method of claim 37, further comprising the step of varying the degree of local data aggregation or fusion performed on the substrate by the onboard network.

39. The method of claim 38 wherein the degree of local data aggregation or fusion performed on the substrate by the onboard network is varied to:
   (a) tailor the probability of false detection and missed detection, or
   (b) vary data rates along the communication bus or communication buses.

40. The method of claim 18 or 21 wherein a computation regarding a parameter, analyte or characteristic of interest is performed onboard.

41. The method of claim 40 wherein the onboard computation is performed after or before networking.

* * * * *